United States Patent
Velazquez-Figueroa et al.

(10) Patent No.: US 10,883,762 B1
(45) Date of Patent: Jan. 5, 2021

(54) CONTINUOUS GRANULO-DRYER FOR THE MANUFACTURING OF PHARMACEUTICAL PRODUCTS VIA WET GRANULATION

(71) Applicants: Carlos Velazquez-Figueroa, Mayaguez, PR (US); Leonel Quinones-Fontalvo, Mayaguez, PR (US)

(72) Inventors: Carlos Velazquez-Figueroa, Mayaguez, PR (US); Leonel Quinones-Fontalvo, Mayaguez, PR (US)

(73) Assignee: University of Puerto Rico, San Juan, PR (US)

(*) Notice: Subject to any disclaimer, the term of this patent is extended or adjusted under 35 U.S.C. 154(b) by 164 days.

(21) Appl. No.: 16/249,925

(22) Filed: Jan. 17, 2019

Related U.S. Application Data

(60) Provisional application No. 62/618,415, filed on Jan. 17, 2018.

(51) Int. Cl.
*F26B 17/12* (2006.01)
*A61K 9/16* (2006.01)

(52) U.S. Cl.
CPC .......... *F26B 17/124* (2013.01); *A61K 9/1682* (2013.01)

(58) Field of Classification Search
CPC ...... F26B 17/124; F26B 21/02; F26B 23/022; F26B 3/04; F26B 3/06; F26B 3/14; F26B 3/26; F26B 17/12; F26B 17/1408; F26B 3/08; F26B 3/082; F26B 3/22; F26B 3/225; F26B 17/00; A61K 9/1682

USPC .................. 34/168, 169, 165, 166
See application file for complete search history.

(56) References Cited

U.S. PATENT DOCUMENTS

| | | | | |
|---|---|---|---|---|
| 640,628 | A * | 1/1900 | Bussells | F26B 23/022 34/79 |
| 3,646,688 | A * | 3/1972 | Osterman | F26B 17/1483 34/168 |
| 3,693,893 | A * | 9/1972 | McIntyre | B02C 18/08 241/258 |
| 4,223,452 | A * | 9/1980 | Chambers | F26B 3/00 34/413 |
| 4,270,553 | A * | 6/1981 | Conrad | A24B 3/182 131/291 |
| 4,787,152 | A * | 11/1988 | Mark | B01J 8/36 34/369 |
| 5,124,100 | A * | 6/1992 | Nishii | B01J 2/16 264/82 |

(Continued)

*Primary Examiner* — Justin M Jonaitis
(74) *Attorney, Agent, or Firm* — Hoglund & Pamias, PSC; Roberto J. Rios

(57) ABSTRACT

The invention provides an efficient equipment that can be easily implemented to dry materials in a continuous manufacturing line of pharmaceutical products without the need of external air or HEPA exhaust filter cartridges. A continuous granulo-dryer for the manufacturing of pharmaceutical products via wet granulation includes a recirculation system that allows to continuously recirculate the air used to dry the materials back into the granulo-dryer. Control systems and sensors are provided to promote a high percentage (up to 98%) of product monitored, an efficient heat and mass transfer between the air and the product avoiding the segregation of the materials and preserving the homogeneity of the Active Principal Ingredient (API).

20 Claims, 1 Drawing Sheet

(56) References Cited

U.S. PATENT DOCUMENTS

| | | | | |
|---|---|---|---|---|
| 5,220,732 A | * | 6/1993 | Lee | F26B 11/028 34/131 |
| 2020/0011528 A1 | * | 1/2020 | Hensel | F23J 15/027 |

* cited by examiner

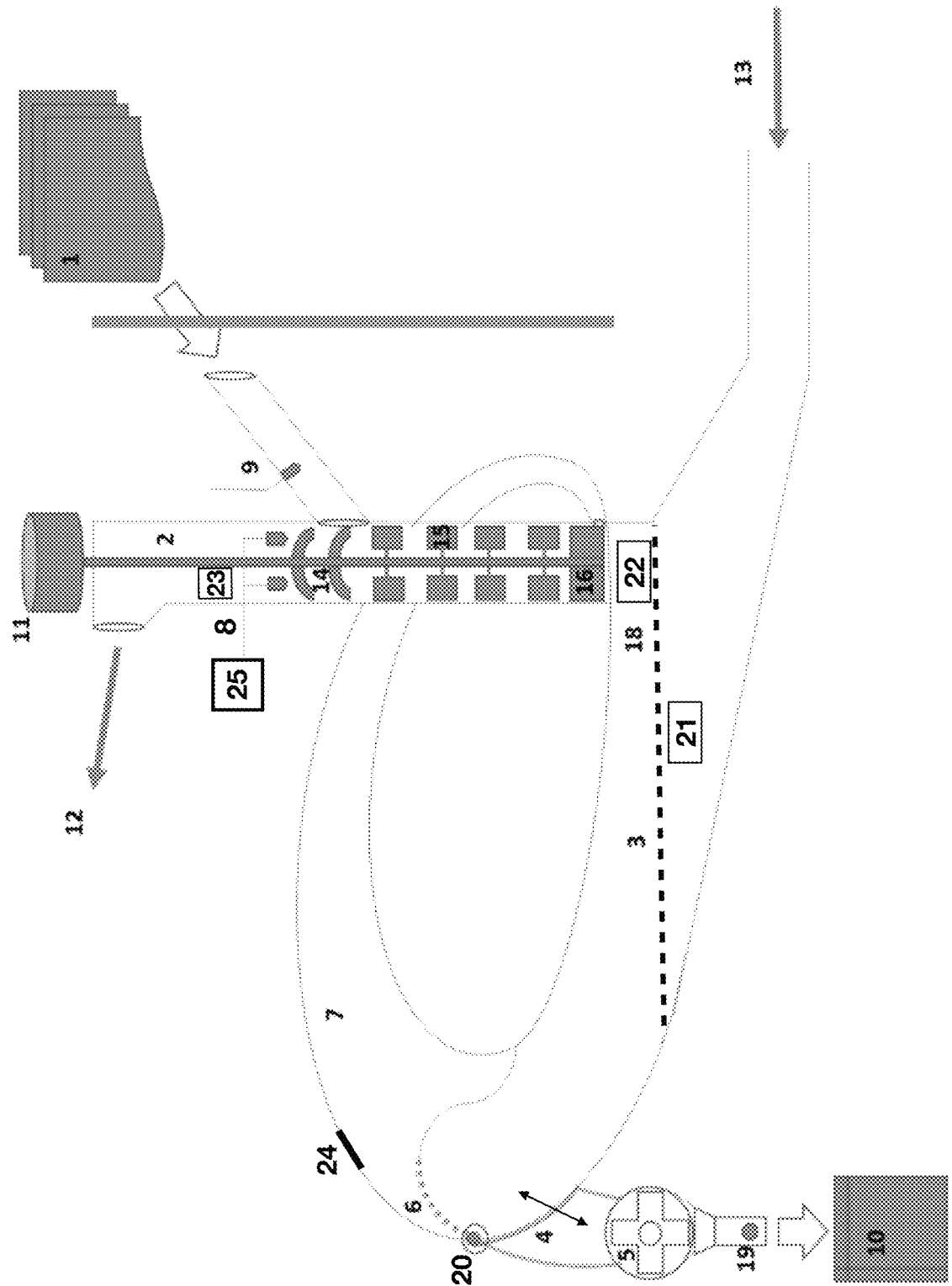

CONTINUOUS GRANULO-DRYER FOR THE MANUFACTURING OF PHARMACEUTICAL PRODUCTS VIA WET GRANULATION

BACKGROUND OF THE INVENTION

Fluid bed granulation is a wet granulation process that involves the addition of a binder liquid to primary particles to form aggregated granulates. The process of granulation improves material properties such as flowability and compressibility and also avoids segregation of mixture components. The material to be granulated is suspended within the fluid bed granulator by applying high-velocity air across the particles in order to set-up a fluidized bed of material. The binder liquid is sprayed upon the primary powder resulting in the particles adhering to each other and forming larger granulates. Upon completion of the spraying process, the wet granulate is dried within the fluid bed granulator using hot air. During the spraying and drying process, granulates will grow in size and then reduce due to inter granulate.

Continuous Fluid Bed Granulators & Dryers are designed to provide higher throughputs as compared to batch systems. Offering the same advantages as seen in the batch systems, continuous systems have been successfully applied in the chemical, detergent, enzyme, food and confectionery industries. However, commercial continuous fluid bed dyers and granulators have issues to monitor and control efficiently Critical Quality Attributes (CQA) of the products, such as homogeneity, particle size distribution and segregation. Some of them require expensive external air (N2 purge) system to clean the interface of the PAT tool and HEPA exhaust filter cartridge.

Thus, there is an unsolved need for a more efficient equipment that can be easily implemented to dry materials in a continuous manufacturing line of pharmaceutical products without the need of external air or HEPA exhaust filter cartridges.

BRIEF DESCRIPTION OF THE DRAWINGS

Further features and advantages of the invention will become apparent from the following detailed description taken in conjunction with the accompanying FIGURES showing illustrative embodiments of the invention, in which:

FIG. 1 shows the continuous granulo-dryer according to the present invention.

Throughout the FIGURES, the same reference numbers and characters, unless otherwise stated, are used to denote like elements, components, portions or features of the illustrated embodiments. The subject invention will be described in detail in conjunction with the accompanying FIGURES, in view of the illustrative embodiments.

DETAILED DESCRIPTION OF THE INVENTION

The invention will be explained in further detail by means of embodiments with reference to the drawing. FIG. 1 shows a schematic overview of a continuous granulating and drying apparatus according to the invention.

In the embodiment shown, the apparatus comprises a vertical granulator 2 coupled to a fluid bed dryer (FBD) 3. The continuous fluid bed dyer/granulator has an inlet 9 preferably in the upper right side for loading the powder materials dispensed from a feeding system 1 and an outlet in the lower left side for delivering the dried granulated material to a compression section 10. The feeding system 1 can provide the material using a single feeding pipe or a plurality of feeding pipes separately providing the particles to be granulated. The vertical granulator 2 includes a rotary shaft 11 coupled to a blade arrangement (14-16). Specifically, blades 14 are provided to compact and direct the powder materials toward the mixing section. Blades 15 are provided to promote mixing the powder material and blades 16 are provided to disperse the material at the exit of the vertical granulator 2 to facilitate the movement towards the FBD 3. A spray nozzle system 8 provided to feed binder is preferably arranged at the top of the vertical granulator 2, above blades 14. The powder ingredients may be supplied to the vertical granulator inlet 9 mixed or separately, and then mixed in the vertical granulator 2. A metal mesh screen can be installed at the outlet of vertical granulator 2.

The continuous fluid bed dryer has a gate valve 4 installed at the outlet of the FBD 3 to improve the stability and controllability of the equipment in terms of Critical Quality Attribute (CQA) of moisture content and the mass flow of the product required for the operation in a continuous manufacturing plant. This gate valve 4 allows the passage of the granulate material to the milling 5 and compression section 10. Another mesh screen 6 is provided between the output of the FBD 3 and the inlet of a recirculation system 7 for recirculating the air from said FBD 3 into the vertical granulator 2 or the FBD 3. Also, the mesh screen 6 can be configured and sized to allow the return of at least some of the granulate material to the vertical granulator 2 using the recirculation system 7, in case the granulated material is out of specification in terms of CQA. A blower may be optionally installed into the recirculation system. The continuous dryer of the present invention has an exhaust air outlet 12 provided at the vertical granulator 2.

The material is dried and transported from right to left by the air flow entering from inlet 13 supplied from the bottom of the dryer. The continuous fluid bed dryer has a unique modular design that facilitates easily removing, installing and replacing at least the air inlet port, the fluid bed dryer compartment, the vertical granulator, and the recirculation system, among others.

The combination of factors, such as the amount of powder material entering the granulator, the size of the metal mesh, the rotation speed of the blades above of the metal mesh, and the recirculated air of the drying section may control the flow rate and particle size of the granulated powder discharged to the dryer.

Process Analytical Technology (PAT) Tool

The PAT control unit is provided to promote a high percentage (up to 98%) of product monitored. The system of the invention provides an efficient heat and mass transfer between the air and the product avoiding the segregation of the materials and preserving the homogeneity of the Active Principal Ingredient (API) based at least on the geometrical configuration of the apparatus and operating parameters and variables.

The continuous dryer of the present invention has a control system that will permit the automatic manipulation of different variables and operating parameters to ensure the best possible behavior of the dryer. For example, one variable to control is the final humidity of the granules or material exiting the dryer. According to an embodiment of the invention, a humidity sensor 20 is installed at the exit of FBD 3 and the gate valve 4 is selectively adjusted to ensure the desired humidity based on measurements from said humidity sensor 20. For example, the valve gate 4 can be moved to a closed or towards a closed position when a humidity higher than a selected humidity level is detected so that the material inside the FBD 3 is allowed to be dried and thus, lowering the humidity level. In addition, a heater 21 is preferably provided in the area between air inlet 13 and the inlet 18 of the FBD 3 to set the temperature of the air entering FBD 3. A temperature sensor 22 is preferably installed at the entrance of FBD 3 to measure the temperature so that the heater 21 is actuated based on the temperature measurements. Another parameter/variable to be controlled is the fluidization of the powders, material or particles being granulated in vertical granulator 2. A fluidization level sensor 23 is preferably installed at the vertical granulator 2 and the air entering at the air inlet 13 will be adjusted to achieve a desired fluidization based on measurements from said fluidization level sensor 23. In addition, a relief valve 24 is preferably installed at the recirculation system 7 to selectively control and adjust the air pressure exiting said recirculation system 7 and entering into said FBD 3 at point 16 to avoid over fluidization. According to an embodiment of the invention, the air exiting recirculation system 7 can directed to a single location on said vertical granulator 2 including an area located at the output of the vertical granulator 2. Alternatively, the output of said recirculation system 7 can be coupled to plural points throughout said vertical granulator 2. Also, a pressure sensor 25 is installed in a binder supply line to ensure the right pressure is being supplied to the feed binder spray nozzle system 8. According to a preferred embodiment, the sprayed binder pressure will be adjusted using a variable speed pump (not shown).

The continuous granulo-dryer of the present invention can be used to dry organic and inorganic materials. A blower can be provided to improve the flow of air through the recirculation system. Additional blowers and/or heaters can be added throughout the dryer to change the distribution of the air flow entering from the bottom of the FBD. A silica-based unit to control humidity of the recirculated air can be used. The size and dimensions of the openings of the mesh screens are selected according to the size of the particles to be granulated and whether the mesh screen is provided to allow or prevent the passage of the particles. In a preferred embodiment, the openings of the mesh screens have a size of 5 μm or less.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A continuous granulo-dryer for the manufacturing of pharmaceutical products via wet granulation comprising:
   a vertical granulator;
   a material inlet coupled to said vertical granulator;
   an inlet of a fluid bed dryer coupled to an outlet of said vertical granulator;
   an air inlet coupled at or adjacent to the inlet of said fluid bed dryer;
   a gate valve provided at an outlet of said fluid bed dryer; and
   an inlet of a recirculation system coupled at or adjacent to the outlet of said fluid bed dryer, wherein an outlet of said recirculation system is coupled at or adjacent to at least one of: said vertical granulator and said inlet of a fluid bed dryer.

2. The continuous granulo-dryer of claim 1, wherein said vertical granulator comprises a feed binder spray nozzle system.

3. The continuous granulo-dryer of claim 1, wherein said vertical granulator comprises a blade arrangement.

4. The continuous granulo-dryer of claim 1, wherein said vertical granulator comprises an exhaust air outlet.

5. The continuous granulo-dryer of claim 1, further comprising a first mesh screen provided between the air inlet and the inlet of said fluid bed dryer; and a second mesh screen provided between the outlet of said fluid bed dryer and the inlet of said recirculation system.

6. The continuous granulo-dryer of claim 5, wherein said first and second mesh screens have openings smaller than particles of a material to be dried.

7. The continuous granulo-dryer of claim 1, wherein said gate valve is selectively controlled to restrict the flow of dried material exiting said fluid bed dryer.

8. The continuous granulo-dryer of claim 5, wherein said first mesh screen allows the passage of air into said fluid bed dryer while preventing particles of a material to be dried to enter said air inlet.

9. The continuous granulo-dryer of claim 5, wherein said second mesh screen allows the passage of air into said recirculation system while preventing particles of a material to be dried to enter said recirculation system.

10. The continuous granulo-dryer of claim 1, further comprising an air blower coupled to said air inlet to direct air into said fluid bed dryer.

11. The continuous granulo-dryer of claim 4, further comprising an air pump coupled to said exhaust air outlet to remove air out of said vertical granulator.

12. The continuous granulo-dryer of claim 7, further comprising a humidity sensor provided at the outlet of said fluid bed dryer so that the flow of the dried material exiting said fluid bed dryer is restricted based on a humidity level at said outlet of the fluid bed dryer.

13. The continuous granulo-dryer of claim 1, further comprising a heater and a temperature sensor, wherein the heater is selectively actuated to control at least one of: the temperature of air entering said fluid bed dryer and the temperature of air already inside said fluid bed dryer based on a temperature measured by said temperature sensor.

14. The continuous granulo-dryer of claim 1, further comprising a fluidization level sensor provided at said vertical granulator, wherein the amount of air entering said fluid bed dryer is selectively controlled based on a fluidization level measured by said fluidization level sensor.

15. The continuous granulo-dryer of claim 1, further comprising a relief valve provided at said recirculation system to adjust the pressure of air provided to said vertical granulator by the outlet of said recirculation system to avoid over fluidization of a material to be dried.

16. The continuous granulo-dryer of claim 2, further comprising a pressure sensor to selectively control the pressure of binder exiting said feed binder spray nozzle system.

17. The continuous granulo-dryer of claim 1, further comprising an air blower provided at said recirculation system to selectively control the flow of air flowing through the recirculation system.

18. The continuous granulo-dryer of claim 1, wherein the outlet of said recirculation system comprises a single outlet.

19. The continuous granulo-dryer of claim 1, wherein the outlet of said recirculation system comprises a plurality of outlets coupled throughout said vertical granulator 2.

20. The continuous granulo-dryer of claim 3, wherein the blade arrangement comprises at least one of: a first plurality of blades to compact and direct a received material towards a mixing section, a second plurality of blades to promote mixing said received material, and a third plurality of blades to disperse the material exiting said vertical granulator.

* * * * *